US011229764B2

(12) United States Patent
Cheung et al.

(10) Patent No.: US 11,229,764 B2
(45) Date of Patent: Jan. 25, 2022

(54) RESPIRATORY HUMIDIFIER COMMUNICATION SYSTEMS AND METHODS

(71) Applicant: Fisher & Paykel Healthcare Limited, Auckland (NZ)

(72) Inventors: Dexter Chi Lun Cheung, Auckland (NZ); Matthew Jon Payton, Auckland (NZ); Peter Alan Seekup, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 562 days.

(21) Appl. No.: 15/979,300

(22) Filed: May 14, 2018

(65) Prior Publication Data
US 2018/0256846 A1   Sep. 13, 2018

Related U.S. Application Data

(63) Continuation of application No. 14/398,437, filed as application No. PCT/NZ2013/000077 on May 1, 2013, now Pat. No. 9,993,608.
(Continued)

(51) Int. Cl.
*A61M 16/16* (2006.01)
*A61G 11/00* (2006.01)
(Continued)

(52) U.S. Cl.
CPC .............. *A61M 16/16* (2013.01); *A61G 11/00* (2013.01); *A61M 16/0003* (2014.02);
(Continued)

(58) Field of Classification Search
CPC .............. A61M 16/16; A61M 16/0003; A61M 16/109; A61M 16/205; A61M 16/026;
(Continued)

(56) References Cited

U.S. PATENT DOCUMENTS 3,076,451 A * 2/1963 Stoner .................... A61G 11/00
                                                              600/22
4,328,793 A * 5/1982 Martin .................... A61G 11/00
                                                              128/205.26
(Continued)

FOREIGN PATENT DOCUMENTS

CN   101225986   7/2008
CN   101541367   9/2009
(Continued)

OTHER PUBLICATIONS

Extended Search Report; European Application No. 13784148.2; dated Nov. 9, 2015; 9 pages.
(Continued)

*Primary Examiner* — Kendra D Carter
*Assistant Examiner* — Jonathan S Paciorek
(74) *Attorney, Agent, or Firm* — Knobbe, Martens, Olson & Bear, LLP

(57) ABSTRACT

A respiratory humidification system includes a humidifier that is capable of electronic communication with one or more other components of the system thereby permitting transfer of data or control signals between the humidifier and other components of the system. In some systems, a flow generator, such as a ventilator, is provided to supply a flow of breathing gas. The humidifier and the flow generator are capable of electronic communication with one another. In some arrangements, an operating mode or parameter of the humidifier to be set or confirmed by the flow generator, either automatically or manually through a user interface of the flow generator. The humidifier can also utilize data provided by the flow generator or other system component, such as an incubator, to set or confirm an operating mode or parameter of the humidifier. In some arrangements, a user
(Continued)

interface of the humidifier can display data from another system component, such as a nebulizer or pulse oximeter.

16 Claims, 9 Drawing Sheets

Related U.S. Application Data

(60) Provisional application No. 61/641,639, filed on May 2, 2012.

(51) Int. Cl.
| | | |
|---|---|---|
| *A61M 16/10* | (2006.01) | |
| *A61M 16/00* | (2006.01) | |
| *A61M 16/20* | (2006.01) | |
| *A61M 16/04* | (2006.01) | |
| *A61M 16/06* | (2006.01) | |
| *A61M 11/00* | (2006.01) | |
| *A61M 16/08* | (2006.01) | |

(52) U.S. Cl.
CPC .... *A61M 16/0051* (2013.01); *A61M 16/0066* (2013.01); *A61M 16/026* (2017.08); *A61M 16/04* (2013.01); *A61M 16/0666* (2013.01); *A61M 16/109* (2014.02); *A61M 16/1075* (2013.01); *A61M 16/205* (2014.02); *A61G 2203/20* (2013.01); *A61G 2203/46* (2013.01); *A61G 2210/90* (2013.01); *A61M 11/00* (2013.01); *A61M 16/0875* (2013.01); *A61M 16/1085* (2014.02); *A61M 16/1095* (2014.02); *A61M 16/161* (2014.02); *A61M 16/162* (2013.01); *A61M 16/201* (2014.02); *A61M 16/208* (2013.01); *A61M 2016/003* (2013.01); *A61M 2016/0039* (2013.01); *A61M 2205/15* (2013.01); *A61M 2205/18* (2013.01); *A61M 2205/3334* (2013.01); *A61M 2205/3348* (2013.01); *A61M 2205/3368* (2013.01); *A61M 2205/35* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/52* (2013.01); *A61M 2205/6018* (2013.01); *A61M 2205/6054* (2013.01); *A61M 2205/6072* (2013.01); *A61M 2230/205* (2013.01); *A61M 2240/00* (2013.01)

(58) Field of Classification Search
CPC .......... A61M 16/0051; A61M 16/0066; A61M 16/04; A61M 16/0666; A61M 16/1075; A61M 16/1085; A61M 16/1095; A61M 16/161; A61M 16/201; A61M 11/00; A61M 16/0875; A61M 16/162; A61M 16/208; A61M 2016/003; A61M 2016/0039; A61M 2205/15; A61G 11/00; A61G 2203/20; A61G 2203/46; A61G 2210/90
See application file for complete search history.

(56) References Cited

U.S. PATENT DOCUMENTS

| | | | | |
|---|---|---|---|---|
| 4,430,994 | A * | 2/1984 | Clawson | A61M 16/16 128/203.27 |
| 4,796,605 | A * | 1/1989 | Sasaki | A61G 11/00 600/22 |
| 4,967,744 | A * | 11/1990 | Chua | A61M 16/1085 128/204.18 |
| 5,365,922 | A * | 11/1994 | Raemer | A61B 5/0833 128/202.22 |
| 5,759,149 | A * | 6/1998 | Goldberg | A61M 16/16 600/22 |
| 6,349,722 | B1 * | 2/2002 | Gradon | A61M 16/109 128/203.17 |
| 2004/0016430 | A1 * | 1/2004 | Makinson | A61M 16/109 128/203.12 |
| 2006/0113690 | A1 | 6/2006 | Huddart et al. | |
| 2007/0079982 | A1 * | 4/2007 | Laurent | A61M 16/08 174/68.1 |
| 2007/0299358 | A1 | 12/2007 | Bertinetti et al. | |
| 2008/0142019 | A1 * | 6/2008 | Lewis | A61M 16/049 128/207.18 |
| 2009/0229606 | A1 | 9/2009 | Tang et al. | |
| 2010/0206308 | A1 | 8/2010 | Klasek et al. | |
| 2011/0023874 | A1 * | 2/2011 | Bath | A61M 16/0816 128/202.22 |
| 2011/0088693 | A1 | 4/2011 | Somervell et al. | |
| 2011/0120462 | A1 | 5/2011 | Tatkov et al. | |
| 2012/0080032 | A1 | 4/2012 | Bordewick et al. | |

FOREIGN PATENT DOCUMENTS

| | | |
|---|---|---|
| CN | 101583394 | 11/2009 |
| EP | 2260895 | 12/2010 |
| EP | 2098260 | 4/2012 |
| WO | WO 2011/136665 | 11/2011 |

OTHER PUBLICATIONS

International Preliminary Report on Patentability; International Application No. PCT/NZ2013/000077; International Filing Date: May 1, 2013.
Office Action with Translation; Chinese Application No. 201380035445.7; dated Jan. 4, 2016; 19 pages.

\* cited by examiner

RESPIRATORY HUMIDIFIER COMMUNICATION SYSTEMS AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to respiratory humidification systems and methods. In particular, the present invention relates to a respiratory humidifier that is capable of electronic communication with other system components, systems including such a humidifier and related methods.

Description of the Related Art

Under certain circumstances it is necessary or desirable to provide a humidified breathing gas to a patient. In such cases, a respiratory humidifier can be used to provide humidified breathing gas to the patient through a breathing circuit and patient interface. In some arrangements, the system provides respiratory assistance to the patient. Accordingly, such a system can include a flow generator, such as a ventilator, to provide a flow of breathing gas to the patient, often at a constant or variable positive pressure. In existing systems, the flow generator, humidifier and other components of the system each typically includes its own sensors and, for some components, a user interface. Generally, each component is set-up independently from the other components and operates its control processes utilizing information collected from its own sensors. Accordingly, it is an object of the invention to at least provide the public with a useful choice.

SUMMARY OF THE INVENTION

An aspect of the present inventions involves the realization by the present inventor(s) that providing for electronic communication between components of a respiratory humidification system would permit improved performance of the individual components of the system and the system as a whole, at a similar cost or at a reduced-cost compared to existing systems. One or more preferred embodiments provide for communication between the humidifier and other components of the system, such as the flow generator. One preferred embodiment of the present invention is a humidifier that is configured for electronic communication with other components of a respiratory humidification system. Other preferred embodiments relate to systems incorporating such a humidifier and related methods.

Preferred embodiments involve a respiratory assistance and/or humidification system that include a humidifier capable of electronic communication with one or more other components of the system thereby permitting transfer of data or control signals between the humidifier and other components of the system. In some systems, a flow generator, such as a ventilator, is provided to supply a flow of breathing gas. The humidifier and the flow generator are capable of electronic communication with one another. In some arrangements, an operating mode or parameter of the humidifier to be set or confirmed by the flow generator, either automatically or manually through a user interface of the flow generator. The humidifier can also utilize data provided by the flow generator or other system component, such as an incubator, to set or confirm an operating mode or parameter of the humidifier. In some arrangements, a user interface of the humidifier can display data from another system component or the user interface can be configured to control the other system components, such as a nebulizer or pulse oximeter.

A preferred embodiment involves a respiratory humidification system. The system includes a flow generator that is configured to deliver a flow of breathing gas. A humidifier receives the flow of breathing gas from the flow generator and outputs a humidified flow of breathing gas. A breathing circuit receives the flow of humidified breathing gas from the humidifier and a patient interface receives the flow of humidified breathing gas from the breathing circuit. The patient interface delivers the flow of humidified breathing gas to a patient. A communication connection between the humidifier and the flow generator is configured to permit electronic communication between the humidifier and the flow generator.

In some configurations, the flow generator automatically sets an operating parameter or mode of the humidifier based on an operating parameter or mode of the flow generator.

In some configurations, the flow generator comprises a user interface, which is configured to permit a user to set an operating parameter or mode of the humidifier using the user interface of the flow generator. The flow generator can provide a prompt on the user interface for the user to set the operating parameter or mode of the humidifier. The setting of the operating parameter or mode can comprise confirming a default mode of the humidifier.

In some configurations, the humidifier automatically sets an operating parameter or mode of the humidifier based on an operating parameter or mode of the flow generator. The operating parameter of the flow generator can comprise the flow rate of the flow of breathing gas.

In some configurations, the system can include a communication connection between the humidifier and the breathing circuit, which is configured to permit electronic communication between the breathing circuit and the humidifier. The breathing circuit can communicate breathing circuit data to the humidifier, wherein the humidifier can communicate the breathing circuit data to the flow generator, and wherein the flow generator sets an operating parameter or mode based on the breathing circuit data. The breathing circuit data can be automatically communicated to the humidifier when the breathing circuit is connected to the humidifier.

In some configurations, the flow generator is configured to communicate with a central monitoring system or electronic patient data recordation system, wherein the flow generator is configured to communicate the operating parameter or mode of the humidifier to the central monitoring system or electronic patient data recordation system.

In some, configurations, the system further comprises a temperature regulation device and a communication connection configured to permit electronic communication between the temperature regulation device and the humidifier. The data relating to the temperature regulation device can be communicated to the humidifier and the humidifier can set an operating parameter or mode based on the data relating to the temperature regulation device. The temperature regulation device can be an incubator and the data relating to the temperature regulation device can comprise a temperature level. The humidifier can be located outside of the incubator, the patient interface can be located within the incubator, and the breathing circuit can extend between the humidifier and the patient interface, the breathing circuit can comprise a first portion located outside of the incubator and a second portion located within the incubator, a first heating element can be configured to apply heat energy to the first portion, a second heating element can be configured to apply heat energy to the second portion, and a sensor can be configured to detect a parameter of the flow of humidified breathing gas, the sensor can be located within the first portion, wherein the humidifier can control the first heating element and the second heating element utilizing data from the sensor and data from the incubator. The data from the sensor can comprise one or more of: a flow rate and a temperature of the flow of humidified breathing gas. The data from the incubator can comprise one or more of: a current temperature and a set-point temperature of the incubator.

In some configurations, the system can further comprise a peripheral device and a communication connection configured for electronic communication between the peripheral device and the humidifier. The humidifier can set an operating parameter or mode of the humidifier based on data from the peripheral device. The humidifier can comprise a user interface and the humidifier can display data from the peripheral device on the user interface. The humidifier can be configured to permit a user to set an operating parameter or mode of the peripheral device using the user interface. The peripheral device can be a nebulizer or a pulse oximeter.

A preferred embodiment relates to a respiratory humidification system including a humidifier that outputs a humidified flow of breathing gas. A breathing circuit receives the flow of humidified breathing gas from the humidifier. A patient interface receives the flow of humidified breathing gas from the breathing circuit and delivers the flow of humidified breathing gas to a patient. The system also includes a temperature regulation device and a communication connection configured to permit electronic communication between the temperature regulation device and the humidifier.

In some configurations, the humidifier further comprises a user interface, wherein the system is configured such that a user can set an operating parameter or mode of the temperature regulation device using the user interface of the humidifier. The data relating to the temperature regulation device can be communicated to the humidifier and the humidifier can set an operating parameter or mode based on the data relating to the temperature regulation device. The temperature regulation device can be an incubator. The humidifier can be located outside of the incubator, the patient interface can be located within the incubator, and the breathing circuit can extend between the humidifier and the patient interface, the breathing circuit can comprise a first portion located outside of the incubator and a second portion located within the incubator, a first heating element can be configured to apply heat energy to the first portion, a second heating element can be configured to apply heat energy to the second portion, and a sensor can be configured to detect a parameter of the flow of humidified breathing gas, the sensor can be located within the first portion, wherein the humidifier can control the first heating element and the second heating element can utilize data from the sensor and data from the incubator. The temperature regulation device can be an incubator, and the system can further comprise a sensor located within the breathing circuit and configured to detect a parameter of the flow of humidified breathing gas, wherein the data from the sensor can comprise one or more of: a flow rate and a temperature of the flow of humidified breathing gas. The data from the incubator can comprise one or more of: a current temperature and a set-point temperature of the incubator.

A preferred embodiment involves a respiratory humidification system including a humidifier that outputs a humidified flow of breathing gas. A breathing circuit receives the flow of humidified breathing gas from the humidifier. A patient interface receives the flow of humidified breathing gas from the breathing circuit and delivers the flow of humidified breathing gas to a patient. The system also includes a peripheral device and a communication connection configured to permit electronic communication between the peripheral device and the humidifier.

In some configurations, the humidifier sets an operating parameter or mode of the humidifier based on data from the peripheral device. The humidifier can comprise a user interface and the humidifier can display data from the peripheral device on the user interface. The humidifier can be configured to permit a user to set an operating parameter or mode of the peripheral device using the user interface. The peripheral device can be a nebulizer or a pulse oximeter.

In some configurations, the peripheral device can be a flow generator or a temperature regulation device. The flow generator can automatically set an operating parameter or mode of the humidifier based on an operating parameter or mode of the flow generator.

In some configurations, the flow generator comprises a user interface, which is configured to permit a user to set an operating parameter or mode of the humidifier using the user interface of the flow generator. The flow generator can provide a prompt on the user interface for the user to set the operating parameter or mode of the humidifier. The setting of the operating parameter or mode can comprise confirming a default mode of the humidifier.

In some configurations, the humidifier automatically sets an operating parameter or mode of the humidifier based on an operating parameter or mode of the flow generator. The operating parameter of the flow generator can comprise the flow rate of the flow of breathing gas.

In some configurations, the system can include a communication connection between the humidifier and the breathing circuit, which is configured to permit electronic communication between the breathing circuit and the humidifier. The breathing circuit can communicate breathing circuit data to the humidifier, wherein the humidifier can communicate the breathing circuit data to the flow generator, and wherein the flow generator sets an operating parameter or mode based on the breathing circuit data. The breathing circuit data can be automatically communicated to the humidifier when the breathing circuit is connected to the humidifier.

In some configurations, the flow generator is configured to communicate with a central monitoring system or electronic patient data recordation system, wherein the flow generator is configured to communicate the operating parameter or mode of the humidifier to the central monitoring system or electronic patient data recordation system.

In some configurations, the data relating to the temperature regulation device can be communicated to the humidifier and the humidifier can set an operating parameter or mode based on the data relating to the temperature regulation device. The temperature regulation device can be an incubator and the data relating to the temperature regulation device can comprise a temperature level. The humidifier can be located outside of the incubator, the patient interface can be located within the incubator, and the breathing circuit can extend between the humidifier and the patient interface, the breathing circuit can comprise a first portion located outside of the incubator and a second portion located within the incubator, a first heating element can be configured to apply heat energy to the first portion, a second heating element can be configured to apply heat energy to the second portion, and a sensor can be configured to detect a parameter of the flow of humidified breathing gas, the sensor can be located within the first portion, wherein the humidifier can control the first heating element and the second heating element utilizing data from the sensor and data from the incubator. The data from the sensor can comprise one or more of: a flow rate and a temperature of the flow of humidified breathing gas. The data from the incubator can comprise one or more of: a current temperature and a set-point temperature of the incubator.

A preferred embodiment relates to a method of operating a respiratory humidifier, including establishing electronic communication between the humidifier and a flow generator that provides a flow of breathing gas to the humidifier, and setting an operating parameter or mode of the humidifier automatically based on an operating parameter or mode of the flow generator.

In some cases, the flow generator directs the setting of the operating parameter of the humidifier. The setting of the operating parameter of the humidifier can be done by the humidifier based on the operating parameter or mode of the flow generator.

In some cases, the method further comprises transmitting breathing circuit data relating to a parameter of a breathing circuit to the humidifier over an electronic communication connection, transmitting the breathing circuit data to the flow generator, and setting an operating parameter or mode of the ventilator based on the breathing circuit data. The transmitting of the breathing circuit data to the humidifier can occur automatically upon connection of the breathing circuit to the humidifier.

In some cases, the method further comprises transmitting data relating to the humidifier to a central monitoring system or an electronic patient data recordation system through the flow generator. The method can further comprise delivering the flow of humidified breathing gas to a patient interface located within an incubator, and setting an operational parameter or mode of the humidifier based on data transmitted to the humidifier from the incubator relating to an operation parameter or mode of the incubator.

A preferred embodiment involves a method of operating a respiratory humidifier, including establishing electronic communication between the humidifier and a flow generator that provides a flow of breathing gas to the humidifier, and setting an operating parameter or mode of the humidifier using a user interface of the flow generator.

In some cases, the method further comprises transmitting breathing circuit data relating to a parameter of a breathing circuit to the humidifier over an electronic communication connection, transmitting the breathing circuit data to the flow generator, and setting an operating parameter or mode of the ventilator based on the breathing circuit data. The transmitting of the breathing circuit data to the humidifier can occur automatically upon connection of the breathing circuit to the humidifier. The method can further comprise transmitting data relating to the humidifier to a central monitoring system or an electronic patient data recordation system through the flow generator. The method can further comprise delivering the flow of humidified breathing gas to a patient interface located within an incubator, and setting an operational parameter or mode of the humidifier based on data transmitted to the humidifier from the incubator relating to an operation parameter or mode of the incubator.

A preferred embodiment involves a method of operating a respiratory humidifier, including establishing electronic communication between the humidifier and an incubator, delivering a flow of humidified breathing gas from the humidifier to a patient interface located within the incubator, and setting an operating parameter or mode of the humidifier using data transmitted to the humidifier from the incubator relating to an operation parameter or mode of the incubator.

In some cases, the method further comprises setting an operation parameter or mode of the incubator using a user interface of the humidifier.

A preferred embodiment relates to a method of operating a respiratory humidifier, including establishing electronic communication between the humidifier and a peripheral device, transmitting peripheral device data from the peripheral device to the humidifier, the peripheral device data comprising an operating parameter or mode of the peripheral device, and displaying the peripheral device data on a user interface of the humidifier.

In some cases, the method further comprises setting an operating parameter or mode of the peripheral device using the user interface of the humidifier. The method can further comprise setting an operating parameter or mode of the humidifier based on the peripheral device data.

BRIEF DESCRIPTION OF THE DRAWINGS

Preferred embodiments having certain features, aspects and advantages of the present invention are described with reference to the accompanying drawings, which are intended to illustrate and not to limit the invention. The drawings contain thirteen (13) figures.

DETAILED DESCRIPTION OF THE PREFERRED EMBODIMENT

One or more embodiments of the respiratory humidification components, systems and related methods disclosed herein provide for electronic communication between two or more components of the system. In at least one arrangement, data relating to an operating mode or parameter of a first system component is communicated to a second system component, which can utilize the data to set or confirm an operating mode or parameter of the second system component or another system component. In at least one arrangement, the communication of data between a first system component and a second system component provides for the user interface of one of the first or second system components to display or record data relating to, or allow the control of, the other of the first or second system components. In at least one arrangement, a first system component can be connected to a second system component and obtain data regarding the second system component. The first system component can then communicate the data to a third system component, which can use the data to set or confirm an operating parameter or mode of the third system component. In at least one arrangement, a first system component can be connected to a second system component and obtain data regarding the second system component. The first system component can then use the data to set or confirm an operating parameter or mode of a third system component. Examples of such systems and methods are disclosed herein and are intended to illustrate, and not to limit, certain features, aspects and advantages of the present invention.

Figure 1:
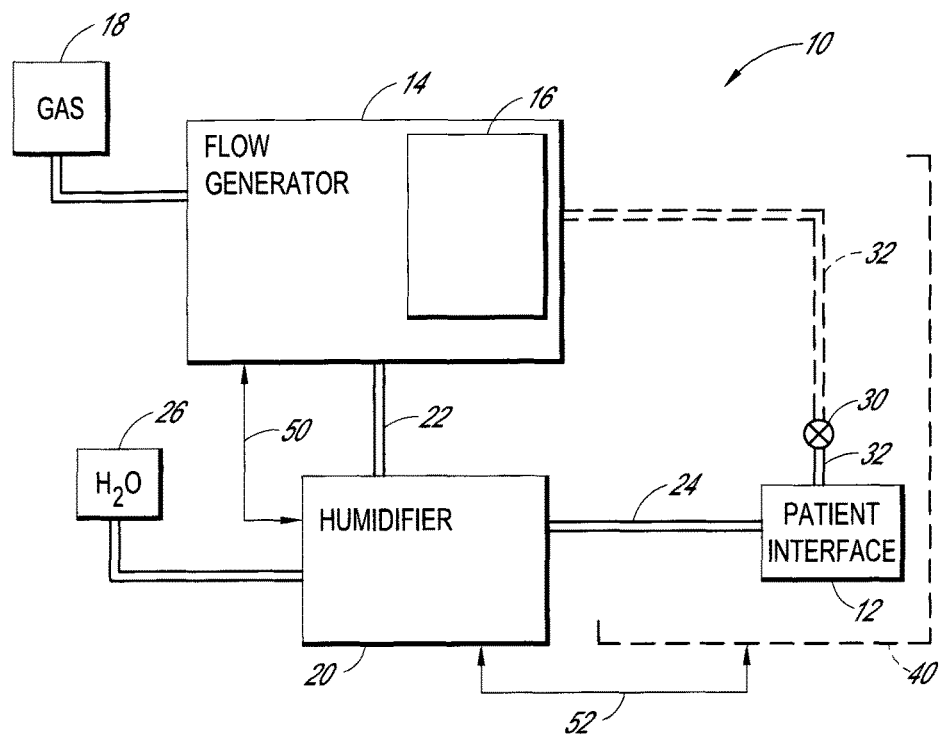
FIG. 1 illustrates a respiratory humidification system having certain features, aspects and advantages of the present invention. The illustrated respiratory humidification system includes a gas flow generator, a humidifier and a breathing circuit.

FIG. 1 illustrates a respiratory humidification system, which is generally referred to by the reference number 10. The system 10 preferably provides a flow of humidified breathing gas to a user or patient (not shown) through an appropriate patient interface 12 and provides for communication of system data between two or more components of the system 10. The illustrated system 10 includes a flow generator 14 that can provide a flow of a suitable breathing gas. In the illustrated arrangement, the flow generator 14 is a ventilator that can provide air, oxygen or an air/oxygen mixture to the patient interface 12 at a continuous or variable pressure above ambient pressure. Accordingly, the flow generator 14 is also referred to as a ventilator herein. Preferably, the ventilator 14 is an electronic ventilator that includes electronic or computer control of certain ventilator functions, such as the timing, pressure, volume or flow rate of the breathing gas supplied by the ventilator 14. The ventilator 14 also includes a memory for storing relevant ventilator data and operating protocols.

Preferably, the ventilator 14 also includes a user interface 16 that displays ventilator operating data and information. Preferably, the user interface 16 also permits a user to interact with the ventilator 14 by entering data or information, or setting or confirming various operating settings or modes of the ventilator 14. The user interface 16 can be of any suitable arrangement, including a display screen in combination with user inputs, such as buttons, knobs, keys, a navigation ring and the like. In one preferred arrangement, the user interface 16 can be a touch screen capable of displaying information and receiving user inputs. The touch screen can be the only user input, or can be used in combination with other user inputs, such as those previously described.

In the illustrated system 10, a source of breathing gas 18, which can be a gas cylinder, a wall supply or any other suitable source of breathing gas, is connected to the ventilator 14. The breathing gas can be air, oxygen, a blend of air and oxygen, or any other suitable gas for use in respiratory therapy, such as hydrogen, helium or nitrogen. In some embodiments, the ventilator 14 utilizes room air or ambient air alone or in combination with a gas from the source of breathing gas 18 to create a flow of breathing gas. The ventilator 14 preferably is capable of precisely blending the ambient air and the breathing gas from the source of breathing gas 18 and delivering the blended air and gas (collectively referred to as "breathing gas") in accordance with a desired value or range of one or more parameters, such as pressure, volume, flow rate or time. In other embodiments, the flow generator 14 does not utilize ambient or room air.

The flow of breathing gas outputted from the ventilator 14 preferably is delivered to a humidifier system, or humidifier 20, by a suitable conduit, such as an inspiratory tube or supply tube 22. The humidifier 20 provides humidity or vaporized liquid, such as water, to the flow of breathing gas received from the ventilator to output a flow of humidified breathing gas to the patient interface 12 through a suitable conduit, such as a supply tube 24. Preferably, the humidifier 20 can output a flow of humidified breathing gas at a set-point or desired temperature and absolute or relative humidity, such as an optimal temperature of about 37 degrees Celsius and absolute humidity of about 44 mg/L or relative humidity of 100%, or within a desirable or acceptable range of the optimal temperature and absolute or relative humidity. For example, an acceptable range of the absolute humidity may be any value at or above about 33 mg/L or a corresponding relative humidity of about 74.85% at 37 degrees Celsius.

The humidifier 20 can include a humidifier unit and a humidity chamber. The humidity chamber can hold a volume of liquid, such as water, which is heated by the humidifier unit to create a vapor within the humidity chamber that is transferred to the flow of breathing gas. The humidity chamber can be an auto-fill variety, in which a source of liquid 26 is connected to the humidity chamber to refill the volume of liquid, as appropriate. An example of the basic construction and operation principles of the humidifier unit is the MR850 Humidifier sold by Fisher & Paykel Healthcare Ltd., the Assignee of the present application. A suitable humidity chamber is the MR225 or MR290 humidity chamber sold by the Assignee of the present application. However, as described herein, the present humidifier 20 is also configured for electronic communication with one or more of the components of the system 10, preferably including the ventilator 14 or other flow generator.

The supply tube 24 can be a heated supply tube such that a temperature of the flow of breathing gas is maintained at an elevated level within the supply tube 24 and to avoid or limit condensation within the supply tube 24 or patient interface 12. The supply tube 24 can include a heating element that is connected to a power or heat source. Preferably, the humidifier 20 is configured to power the heating element. A sensor or probe (not shown in FIG. 1) can be coupled to the humidifier 20 and supply tube 24 to detect a parameter of the flow of humidified breathing gas, such as the temperature and/or flow rate of the flow of breathing gas through the supply tube 24. Preferably, the sensor is spaced from the inlet end of the supply tube 24 and, in some arrangements, can be located at the outlet end of the supply tube 24. The sensor can be coupled to the humidifier 20 to transmit sensor data (e.g., temperature and/or flow rate) to the humidifier 20. The humidifier 20 can utilize information from the sensor 48 to control the operating parameters of the humidifier 20, such as a power level of a heating plate or element to, for example, maintain the temperature and/or humidity of the flow of breathing gas within the supply tube 24 at a desirable level or within a desirable or acceptable range.

From the humidifier 20, the flow of humidified breathing gas is supplied to the patient interface 12, which can be any suitable type of interface capable of supplying a breathing gas to the respiratory system of the patient. For example, the interface 12 can be a face mask that covers both the nose and mouth of the patient or a nasal mask that covers only the nose of the patient. Other suitable patient interfaces 12 can also be used, such as a nasal interface, which can include nasal cannula, nasal prongs or other structures that are inserted into the nares of the patient or an appropriate interface device, such as a catheter mount, in combination with an endotracheal tube, tracheostomy (trach) tube, or other invasive interface.

In some embodiments, the interfaces 12 provide a sealed or substantially sealed system that delivers the flow of breathing gas to the patient and receives expiratory gases from the patient. Preferably, the system 10 is a biased flow system in which breathing gas is constantly flowing within the system 10 generally in a direction from the inlet of the patient interface 12 to the outlet of the patient interface 12. Thus, the patient can inhale a portion of the flow of breathing gas and the remainder is passed through the patient interface 12. Exhaled or expiratory gases can mix with the flow of breathing gas and exit the patent interface 12 along with the unused portion of the flow of breathing gas. For convenience, the gases exiting the patient interface 12 are referred to as expiratory gases or the flow of breathing gas, although it is understood that either or both of patient exhaled gases and unused breathing gases can be present at any particular point in time.

In some applications, such as neonatal applications, for example, expiratory gases flow from the patient interface 12 to an optional expiratory pressure device 30, which is configured to regulate the minimum pressure within the system 10, preferably to a level above ambient or atmospheric pressure. Preferably, the expiratory pressure device 30 is connected to the patient interface 12 by a suitable conduit, such as an expiratory tube 32. The expiratory pressure device 30 can be of any suitable arrangement depending on the particular system 10, type of flow generator 14 or therapy protocol. For example, the expiratory pressure device 30 can be an expiratory valve or exhalation port, which regulates the exit of expiratory gases from the system 10. The expiratory valve 30 can be located remotely from the flow generator 14 or can be located at or can be integral with the flow generator, in which case the expiratory tube 32 can extend to the flow generator 14 as illustrated by the dashed lines in FIG. 1 (and other figures herein). In an alternative arrangement, the expiratory pressure device 30 can be connected directly to or integrated with the patient interface 12.

Preferably, the expiratory pressure device 30 is configured to provide a minimum pressure or minimum backpressure within the system 10 and, in particular, at the patient interface 12, which can be referred to as the positive end expiration pressure (PEEP). In some systems, the PEEP is generally equivalent or equivalent to the continuous positive airway pressure (CPAP). Accordingly, such a device 30 can be referred to as a CPAP generator. In some arrangements, the expiratory pressure device 30 can be an oscillatory valve capable of providing pressure oscillations relative to a mean PEEP pressure. One type of oscillating pressure expiratory pressure device 30 is a fluid resistance valve, in particular a liquid or water resistance valve, which is often referred to as a bubbler. In general, a water resistance valve delivers the expiratory gases to an outlet that is submerged in a water reservoir resulting in a resistance to the exit of the expiratory gases that is greater than that caused by ambient or atmospheric pressure and related to the depth of the outlet relative to a surface of the water within the water reservoir. In some arrangements, the depth of the outlet is adjustable to allow the PEEP to be adjusted to a desired level. One suitable bubbler is the Bubble CPAP generator sold by the Assignee of the present application. Additional details of a suitable bubbler device are described in U.S. Pat. No. 6,805,120, which is incorporated by reference herein in its entirety. Preferably, the bubbler (or other oscillatory pressure device) is capable of producing vibrations in the patient's chest at a frequency of between about 5-30 Hz.

However, the expiratory pressure device 30 is not necessary and, in many applications, can be omitted. The expiration gases can be exhausted from the system 10 in any suitable manner by any suitable arrangement, such as a simple exhalation port that may, or may not, regulate or assist in regulating the pressure within the system 10. In some arrangements, the expiratory tube 32 can extend from the patient interface 12 to the ventilator 14 without incorporating the expiratory pressure device 30. An exhalation port or valve can be incorporated in the ventilator 14 to regulate the discharge of the expiration gases in any appropriate manner. For example, the exhalation port or valve can have a closed position in which expiration gases cannot be discharged and an open position in which expiration gases can be discharged, with or without substantial resistance.

The illustrated system 10 can be considered to have an inspiratory circuit and an expiratory circuit. In the illustrated arrangement, the inspiratory circuit can include all or portions of the flow generator 14 (and source of breathing gas 18), the supply tube 22, the humidifier 20, and the supply tube 34. The expiratory circuit can include all or portions of the expiratory tube 32 and the optional expiratory pressure device 30. A portion of the patient interface 12 can be predominantly occupied by a flow of inspiratory breathing gas prior to inspiration by the patient or prior to availability to the patient, while another portion of the patient interface 12 can be predominantly occupied by a flow of expiratory gas exhaled by the patient or that has bypassed the patient. Accordingly, the patient interface 12 can be considered to form a part of each of the inspiratory circuit and the expiratory circuit. A portion of the patient interface 12 can also include a mixture of inspiratory gas and expiratory gas, at least for certain time durations, and may not be considered part of either of the inspiratory circuit or the expiratory circuit or may be considered as a part of each.

Certain portions of the system 10 can be referred to as a breathing circuit, which is generally indicated by the reference number 40. Typically, the breathing circuit 40 includes at least the conduit or tubing that transmits the flow of breathing gas between the components of the system 10. In some cases, the breathing circuit can also include the patient interface 12 and/or the humidifier 20 or portions thereof (e.g., the humidifier chamber). In the illustrated arrangement, the breathing circuit 40 can include one or more of the supply tube 22, the supply tube 24 and the expiratory tube 32. The tubes 22, 24, 32 of the breathing circuit 40 can be corrugated tubes, or tubes constructed from a flexible plastic material, which can be reinforced with a reinforcing structure, such as a spiral wound reinforcing member. The tubes 22, 24, 32 of the breathing circuit 40 can be somewhat resilient in nature, which can result in the tubes 22, 24, 32 flexing or deforming (e.g., expanding and contracting) in response to pressure changes within the system 10. This deformation of the tubes 22, 24, 32 causes the total volume of the breathing circuit 40 to vary in response to the system pressure, which is referred to as the "compliance" of the breathing circuit 40. The compliance of the particular breathing circuit 40 is useful information to assist the flow generator 14 in precisely controlling the delivery of the breathing gas because the change in volume of the system 10 could otherwise be interpreted as breathing gas that is being utilized by the patient.

Another characteristic of the system 10 that is useful information to assist the flow generator 14 in precisely controlling the delivery of the breathing gas is the leak rate of the system 10. The leak rate is the rate of loss of breathing gas from the system 10 as a result of leaks between components of the system 10, between the patient interface 12 and the patient, or other system losses. The total leak rate can be broken down into leak rate portions within various portions of system 10. In particular, a determination or estimation of the leak rate within the breathing circuit 40 can be useful information to assist the flow generator 14 in precisely controlling the delivery of the breathing gas. The leak rate for a particular breathing circuit 40 could be estimated, such as based on a theoretical calculation or actual measurement of a sample size of the breathing circuit model. The leak rate for a particular breathing circuit 40 could also be measured at the time of manufacture.

The breathing circuit 40 can also include a portion that handles both inspiratory flow and expiratory flow of breathing gas. The volume of such a portion defines a dead space of the breathing circuit 40, which is also useful information to assist the flow generator 14 in precisely controlling the delivery of the breathing gas by permitting the flow generator 14 to determine the actual volume of breathing gas utilized by the patient. Some or all of the information regarding the breathing surface 40, such as the compliance, leak rate and dead space, can be provided with the breathing circuit 40, preferably in electronic or electronically-readable form, such as some type of non-volatile memory (EEPROM, RFID, barcode, etc.), for use by the system 10 as described below.

Preferably, the system 10 is configured to permit electronic communication between two or more components of the system 10. In the illustrated arrangement, the humidifier 20 and the flow generator or ventilator 14 are capable of electronic communication through a communication connection 50. Similarly, the humidifier 20 and the breathing circuit 40 are capable of electronic communication through a communication connection 52. The communication connections 50, 52 can be of any suitable arrangement, including a wired connection or wireless connection and utilizing any suitable communication protocol. The communication connection 50, 52 can be direct between the system components or indirect (e.g., through other system components or over a network, such as a Wi-Fi network).

With such an arrangement, information can be transmitted between the humidifier 20 and the breathing circuit 40 or between the humidifier 20 and the ventilator 14. For example, information relating to the breathing circuit 40 can be transmitted to the humidifier 20, which can be used by the humidifier 20 to set or confirm one or more operating parameters or operating modes of the humidifier 20. The information relating to the breathing circuit 40 could also be provided by the humidifier 20 to the ventilator 14, which can utilize the information to set or confirm one or more operating parameters or operating modes of the ventilator 14. Information relating to the humidifier 20 can also be communicated to the ventilator 14 for a similar purpose.

In some arrangements, the communication connections 50, 52 can allow control signals to be transmitted between various components of the system 10 to permit one component to control another component. For example, the ventilator 14 can set or confirm one or more operating parameters or operating modes of the humidifier 20. The ventilator 14 can control the humidifier 20 automatically or can allow a user of the system 10 to set or confirm one or more operating parameters or operating modes of the humidifier 20 utilizing the user interface 16. Information or data transmitted between the components of the system 10 can be any type of information that is relevant to the operation of the system 10, including the on/off power state of a component, the current operational status of a component, current sensor data, and parameter set-points, for example.

Figure 2:
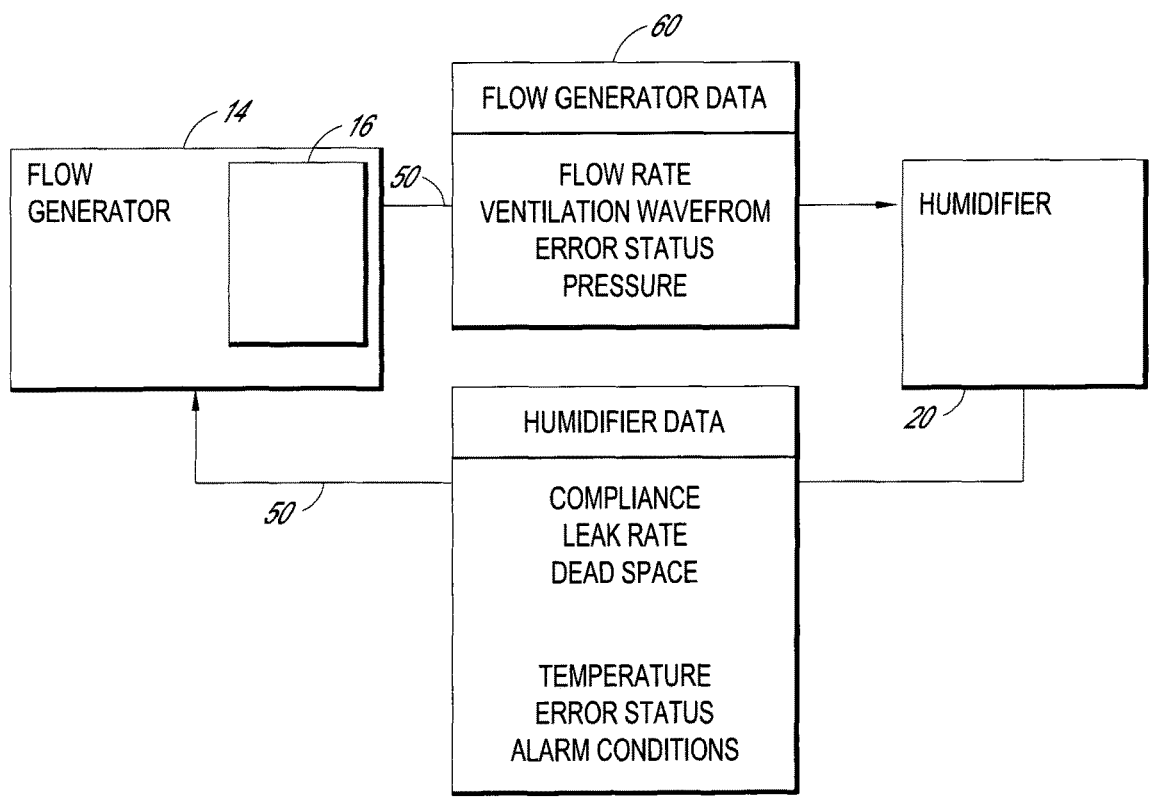
FIG. 2 illustrates a data communication connection between the flow generator and the humidifier of the respiratory humidification system of FIG. 1.

FIG. 2 illustrates an example of a flow of information between the ventilator 14 and the humidifier 20. As described above, information relating to the ventilator 14 can be transmitted to the humidifier 20 over the communication connection 50. As illustrated in block 60, the information or data relating to the ventilator 14 (or other flow generator) can include any information that is relevant to the operation of the ventilator, such as: flow rate, ventilation waveform (breathing pattern), error status and pressure. The humidifier 20 can utilize this information to assist in the optimization of the operating parameters of the humidifier 20 to provide better humidity generation, breathing circuit condensation management, and improved error detectability. As illustrated in block 62, the information or data relating to the humidifier 20 or the breathing circuit 40 (collectively, the "humidifier data") can be transmitted to the ventilator 14 over the communication connection 50. The humidifier data can include any information relating to the status or operation of the humidifier 20, such as temperature information, error status or alarm conditions, or the compliance, leak rate and dead space of the breathing circuit 40.

Figures 3, 4:
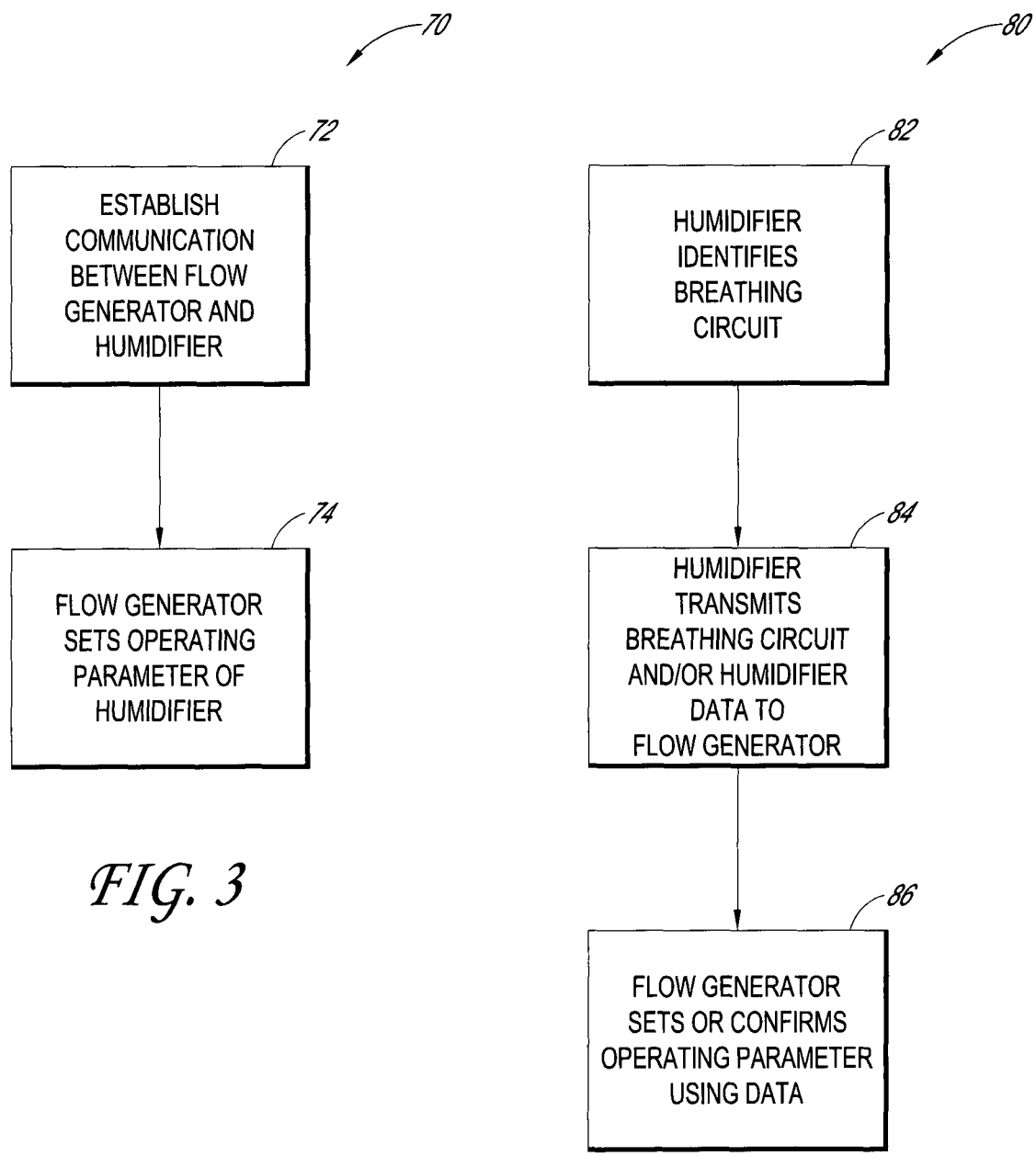
FIG. 3 illustrates a control routine for setting or confirming an operating parameter of the humidifier using the flow generator.
FIG. 4 illustrates a control routine for using the humidifier to send data relating to the breathing circuit to the flow generator for setting or confirming an operating parameter of the flow generator.

With reference to FIG. 3, an example of a process flow or control routine 70 for operating the humidifier 20 with the ventilator 14, or other flow generator, is shown. At block 72, communication is established between the humidifier 20 and the ventilator 14, such as electronic communication via the communication connection 50. Communication can be established at any suitable time using any suitable communication protocol. The communication can be initiated by the ventilator 14, humidifier 20 or another component of the system 10. The communication can be maintained once established or can be initiated and re-established each time the ventilator 14 or humidifier 20 are turned on or powered up, or in response to other occurrences or conditions, such as when the humidifier 20 or other system component has new information to send. In some arrangements, the flow generator 14 and humidifier 20 can be integrated with one another such that a communication channel is always available.

At block 74, the flow generator or ventilator 14 sets (e.g., identifies, reads, selects, adjusts, confirms) an operating parameter of the humidifier 20. The operating parameter can be any parameter or set of parameters that is available or capable of adjustment or selection on the particular humidifier 20 utilized. The operating parameter can include one or more operating modes of the humidifier. The operating parameter(s) or mode(s) can be related to the type of flow generator utilized, such as the ventilator 14, or related to the operating mode of the ventilator 14 or other flow generator.

The operating parameter of the humidifier 20 can be set automatically by the ventilator 14 or manually using the user interface 16. For example, the available operating modes or parameters can be communicated to the ventilator 14 and the ventilator 14 can set the operating mode or operating parameters based on ventilator information or data, such as ventilator type or the ventilator operating mode. With such an arrangement, the humidifier 20 will automatically be placed in an appropriate operating mode for the type of flow generator 14 or type of therapy without additional action by the user of the system 10. In another arrangement, the humidifier 20 could query the ventilator or flow generator 14 for information and set the humidifier 20 operating parameters or mode in response to the ventilator or flow generator 14 information.

Alternatively, the user interface 16 of the ventilator 14 can be utilized to set an operating parameter or operating mode of the humidifier 20. The user interface 16 of the ventilator 14 can replace the user interface of the humidifier 20 or provide an alternative interface. The user interface 16 of the ventilator 14 can include a menu that, displays the available operating parameter(s) or operating mode(s) of the humidifier 20, which can be set by a user through the user interface 16. In some arrangements, a prompt can be displayed on the user interface 16 to direct the user to set an operating parameter or operating mode of the humidifier 20. For example, the humidifier 20 may have a default mode that is inappropriate or undesirable for certain types of flow generators or for certain operating modes of a flow generator. Accordingly, the prompt can increase the likelihood that the user will set the humidifier 20 to an appropriate operating mode. In some cases, the ventilator 14 or other flow generator can remain disabled until the operating parameter(s) or operating mode(s) of the humidifier 20 are set by the user. Such an arrangement avoids a situation in which the humidifier 20 operates in a default mode or the previous mode, which may not be ideal for the current operating mode of the ventilator 14 or other flow generator.

With reference to FIG. 4, a flow process or control routine 80 for providing system data to the ventilator 14 or other flow generator. At block 82, the humidifier 20 identifies the breathing circuit 40 through any suitable arrangement. For example, the humidifier 20 can automatically identify the breathing circuit 40 when the breathing circuit 40 is brought within the proximity or connected to the humidifier 20. Thus, the humidifier 20 and breathing circuit 40 can have a data transfer arrangement that transfers identification data from the breathing circuit 40 to the humidifier 20. The data transfer arrangement can include RFID tags and receivers, electronic pins and receivers, automatic barcode readers, or any other suitable data transfer arrangement. Identification of the breathing circuit 40 could also be accomplished based on the humidifier 20 identifying a property of the breathing circuit. The identification of the breathing circuit 40 could also be accomplished manually, such as with a manual bar code reader or entry of breathing circuit identification information into a user interface of the humidifier 20.

At block 84, the humidifier 20 transmits information or data relating to the breathing circuit 40 and/or information or data relating to the humidifier 20 to the ventilator 14. The breathing circuit data can include: compliance information, leak rate information, dead space information or other relevant information relating to properties, characteristics or operation of the breathing circuit 40 that can assist the ventilator 14 in precisely controlling the delivery of a flow of breathing gas. Humidifier data can include: temperature information, humidity information, chamber volume information or other relevant information relating to properties or characteristics of the humidifier 20 that can assist the ventilator 14 in precisely controlling the delivery of a flow of breathing gas.

At block 86, the ventilator 14 or other flow generator can set or confirm operating parameter(s) or operating mode(s) based on the breathing circuit data and/or the humidifier data. For example, the ventilator 14 can utilize the breathing circuit data to more accurately determine the actual patient tidal volume.

Figure 5:
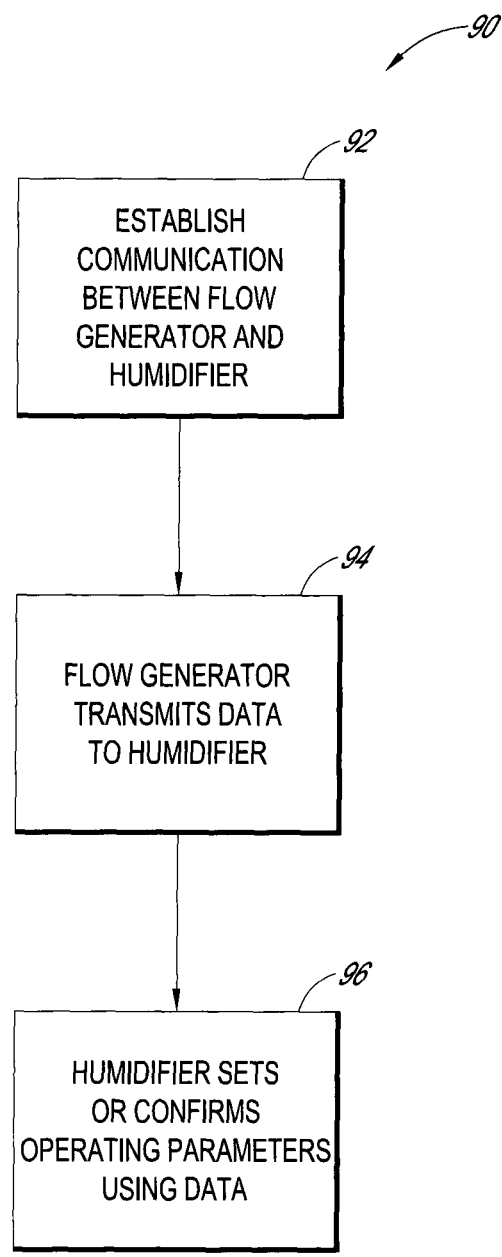
FIG. 5 illustrates a control routine for communicating data relating to the flow generator to the humidifier and setting or confirming an operating parameter of the humidifier using the data.

FIG. 5 illustrates an example of a flow process or control routine 90 for transmitting information relating to the ventilator 14 or other flow generator to the humidifier 20 so that the humidifier 20 can utilize the data to set or confirm operating parameter(s) or operating mode(s). At block 92, communication is established between the ventilator 14 and the humidifier 20. As discussed above in connection with FIGS. 1 and 3, communication can be established through any suitable connection, such as communication connection 50, using any suitable communication process or protocol. Once communication is established between the ventilator 14 and the humidifier 20, at block 94, the ventilator 14 transmits information or data relating to the ventilator 14 to the humidifier 20. The ventilator data can include: flow rate information, waveform (breathing pattern) information, error status information, pressure information or any other relevant information to assist the humidifier 20 in precisely controlling the temperature and/or humidity of the flow of breathing gas delivered from the humidifier 20.

At block 96, the humidifier 20 can utilize the ventilator data to set or confirm operating parameter(s) or operating mode(s) of the humidifier 20 to improve the operation of the humidifier 20. For example, utilizing the ventilator data, the humidifier 20 can provide better humidity generation, breathing circuit condensation management and improve error detectability. Advantageously, such an arrangement can result in improved performance of the humidifier 20 relative to an arrangement in which the humidifier does not receive ventilator data. In most existing arrangements, the humidifier relies on its own sensors to determine information regarding the flow of breathing gas that is relevant to the humidifier functions. Inaccuracies in the measurement of the breathing gas parameters and, thus, inaccuracies in the control of the humidifier can be introduced because of, for example, a lag in the response time of the sensor or as a result of the physical location of the sensor(s). Certain embodiments of the present systems and methods involve the realization that the ventilator 14 also includes sensors to measure parameters relating to the breathing gas to achieve precise control of the flow of breathing gas, and that if this information were shared with the humidifier 20, it could result in improved performance of the humidifier 20.

For instance, the ventilator 14 can output the measured or controlled parameters to the humidifier 20, and the humidifier 20 can control its operations or utilize the information provided by the humidifier 20 sensors in combination with the ventilator data as a feedback control to improve the operation or accuracy of the humidifier 20. For example, the humidifier 20 can adapt one or more of its control parameters, such as proportional, integral and derivative (PID) coefficients, patient-end temperature set-point, heater plate set-point or otherwise operate its heating components (e.g., heater plate and heater wires) or other components using the ventilator data to provide better response and alarm regarding humidity generation and delivery. In one particular application, if the flow of breathing gas is interrupted or stopped, the ventilator 14 can immediately inform the humidifier 20 and the humidifier 20 can respond by shutting off all heating components thereby reducing the chance of delivering overheated gas once the flow resumes. With communication between the ventilator 14 and the humidifier 20, the shutdown of the heating components can occur more quickly than if the humidifier 20 is reliant on its own sensors to determine the interruption or stoppage of gas flow.

Figure 6:
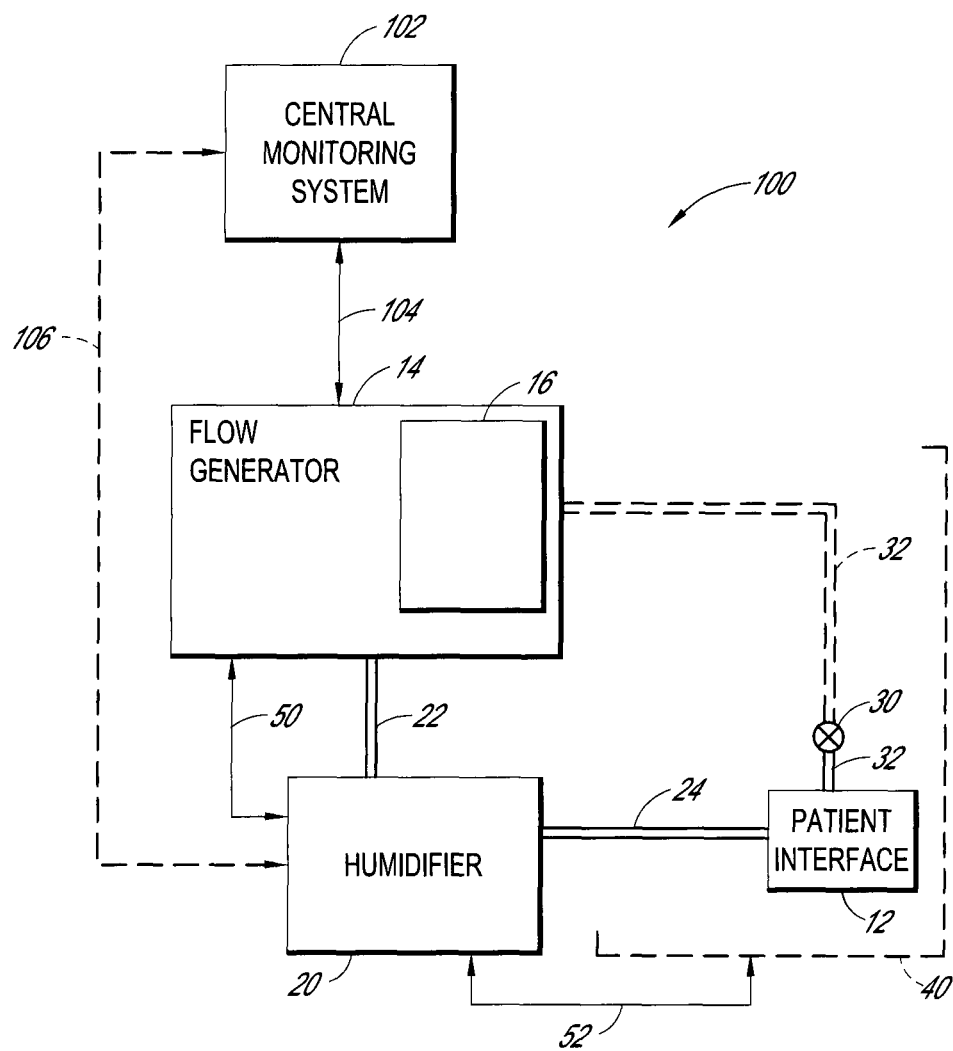
FIG. 6 illustrates a respiratory humidification system, such as a system similar to the system of FIG. 1, which is capable of communicating system data to a central monitoring system or electronic patient data recordation system.

FIG. 6 illustrates a respiratory humidification system 100 that is preferably similar to the system 10 described above. Accordingly, the same reference numbers are used to indicate the same or similar components as in the system 10. The system 100 includes a flow generator, such as a ventilator 14, which has a user interface 16. The ventilator 14 supplies a flow of breathing gas to a humidifier 20 through a supply tube 22. Although not shown, a source of breathing gas can supply breathing gas to the ventilator 14. The humidifier 20 supplies a flow of humidified breathing gas to a patient interface 12 through a supply tube 24. Although not shown, the humidifier 20 can be connected to a source of water or other fluid for refill purposes. The patient interface 12 delivers expiration gases to an expiratory tube 32. An optional expiratory pressure device 30 can be connected to the patient interface 12 by the expiratory tube 32. As described above, if provided, the expiratory pressure device 30 can be located remotely from the ventilator 14 or can be located at or can be integral with the ventilator 14, in which case the expiratory tube 32 can extend to the ventilator 14 as illustrated by the dashed lines in FIG. 6. The breathing circuit 40 can include the supply tubes 22 and 24 along with the expiratory tube 32. Preferably, the ventilator 14 and humidifier 20 are electronically connected for communication with one another by a communication connection 50. Similarly, the humidifier 20 and breathing circuit 40 preferably are electronically connected for communication with one another by a communication connection 52.

The illustrated system 100 is connected for communication with an external memory or monitoring device, such as a central monitoring system 102 by a suitable communication connection 104, which can be wired or wireless. The central monitoring system 102 is usually located remotely from the system 100 and can collect and display information from the system 100 to allow monitoring from the remote location. Typically, the central monitoring system 102 collects and displays data from a plurality of individual patient systems, including those similar to or different from system 100. Thus, the central monitoring system 102 permits remote monitoring of a plurality of patient systems. Although illustrated as a central monitoring system 102, the system 100 can also be configured for communication with other types of external, remote or central systems, such as an electronic patient data recordation system. Electronic patient record keeping is becoming increasingly common and is used for patient diagnostics, fault finding and to supplement or replace paper records. Thus, the system 100 can be configured to publish data to an electronic patient data recordation system. As used herein, references to the central monitoring system 102 also includes other external, remote or central systems, such as an electronic patient data recordation system, unless otherwise noted.

Preferably, the communication connection 104 between the system 100 and the central monitoring system 102 originates from the ventilator 14 on the system 100 end. Thus, preferably, data from the system 100 is communicated to the central monitoring system 102 through the ventilator 14 (or other flow generator). In a respiratory humidification system that includes a ventilator, the humidifier is often viewed as a support device. Thus, the ventilator is more likely to be connected to a central monitoring system than the humidifier. Even if the humidifier is capable of communicating with the central monitoring system, there may not be a connection port available for the humidifier in addition to the ventilator. Even if a connection port is available, in a wired system, separate connection of the ventilator and humidifier results in two cables extending from the system to the connection port(s), which can be inconvenient.

Advantageously, in the illustrated system 100, the ventilator 14 can collect information from the other system components, such as the humidifier 20 or breathing circuit 40, and transmit the information to the central monitoring system 102 along with the ventilator data. Accordingly, the humidifier data or other system data can be included in the information provided to the central monitoring system 102 without requiring the humidifier 20 to be capable of direct communication with the central monitoring system 102. Thus, the monitoring or record-keeping data can be more complete than systems in which only the ventilator data is transmitted. Humidifier or other system data transferred to the central monitoring system 102 through the ventilator 14 can include any normal operation parameters, alarm conditions, duration of use, etc.

In some arrangements, the system 100 can provide for direct communication between the humidifier 20 and the central monitoring system 102, such as via an optional wired or wireless communication connection 106. In such an arrangement, system data can be communicated between the humidifier 20 and the central monitoring system 102. System data can include information related to the humidifier 20 or, in some arrangements, the humidifier 20 can obtain information from other system components such that the system data communicated between the humidifier 20 and the central monitoring system 102 includes information from system components in addition to or other than the humidifier 20. For example, other system components (e.g., the respirator 14 or breathing circuit 40) can provide information to the humidifier 20, which can transmit the system data to the central monitoring system 102 via the communication connection 106.

Figure 7:
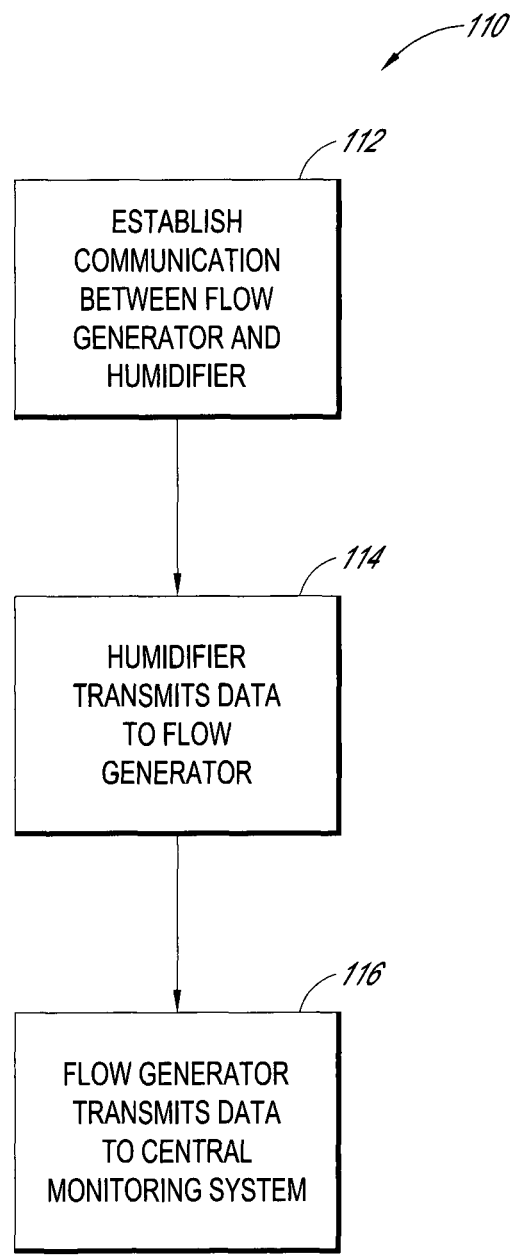
FIG. 7 illustrates a control routine for communicating system data of the system of FIG. 6 from the humidifier to the central monitoring system through the flow generator.

FIG. 7 illustrates an example of a process flow or control routine 110 that can be utilized by the system 100 of FIG. 6 to provide humidifier or other system data to the central monitoring system 102 through the ventilator 14. At block 112, communication is established between the ventilator 14 and the humidifier 20, as described above. At block 114, the humidifier 20 transmits data, such as humidifier data, breathing circuit data or other system data (collectively, the "humidifier data"), to the ventilator 14. At block 116, the ventilator 14 transmits the data to the central monitoring system 102 through the communication connection 104. The ventilator 14 can transmit the humidifier data to the central monitoring system 102 separately from the ventilator data, or the ventilator 14 can aggregate ventilator data and humidifier data and send the data as a single data set. The ventilator 14 can transmit data to the central monitoring system 102 via any suitable communication protocol.

Figure 8:
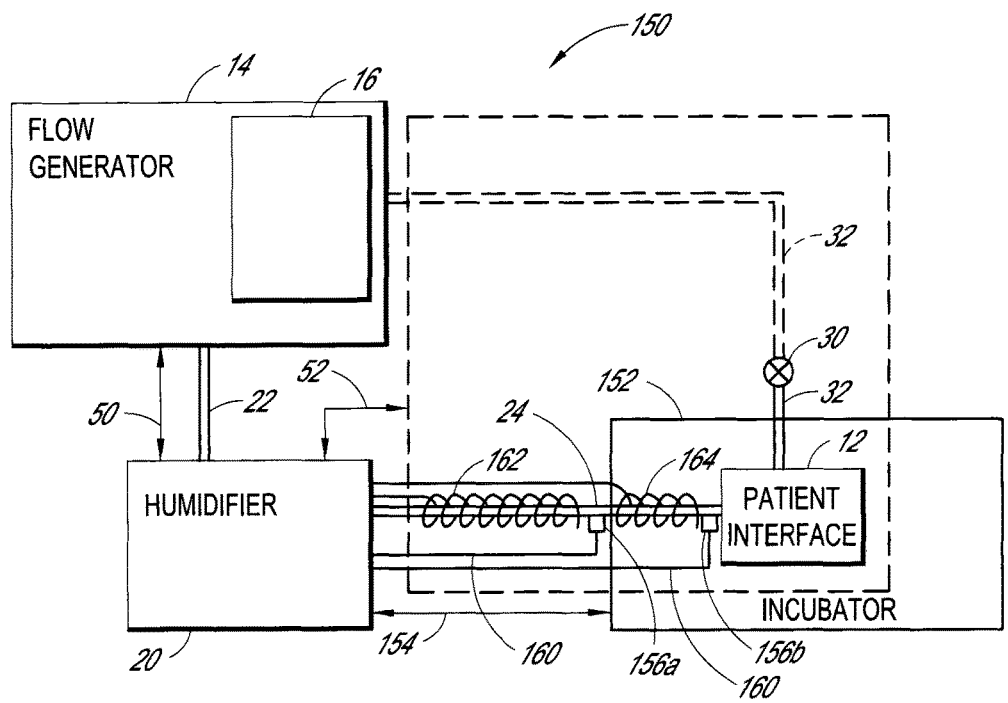
FIG. 8 illustrates a respiratory humidification system, such as a system similar to the system of FIG. 1, which incorporates an incubator.

FIG. 8 illustrates another system 150, which preferably is similar to the systems 10 and 100 described above. Accordingly, the same reference numbers are used to refer to the same or similar components. The system 150 includes a flow generator, such as a ventilator 14, which has a user interface 16. The ventilator 14 supplies a flow of breathing gas to a humidifier 20 through a supply tube 22. Although not shown, a source of breathing gas can supply breathing gas to the ventilator 14. The humidifier 20 supplies a flow of humidified breathing gas to a patient interface 12 through a supply tube 24. Although not shown, the humidifier 20 can be connected to a source of water or other fluid for refill purposes. The patient interface 12 delivers expiration gases to an expiratory tube 32. An optional expiratory pressure device 30 can be connected to the patient interface 12 by the expiratory tube 32. As described above, if provided, the expiratory pressure device 30 can be located remotely from the ventilator 14 or can be located at or can be integral with the ventilator 14, in which case the expiratory tube 32 can extend to the ventilator 14 as illustrated by the dashed lines in FIG. 8. The breathing circuit 40 can include the supply tubes 22 and 24 along with the expiratory tube 32. Preferably, the ventilator 14 and humidifier 20 are electronically connected for communication with one another by a communication connection 50. Similarly, the humidifier 20 and breathing circuit 40 preferably are electronically connected for communication with one another by a communication connection 52.

The illustrated system 150 incorporates a peripheral component or device, such as a temperature regulation device 152 that is configured to regulate the ambient temperature of a region near or surrounding a patient. The environment controlled by the temperature regulation device can completely or partially surround the patient. In the illustrated arrangement, the temperature regulation device is an incubator 152, such as an infant incubator that is capable of regulating the temperature of a space within the incubator 152. The incubator 152 typically provides an environment at an elevated temperature relative to the ambient temperature of the area surrounding the incubator 152. However, other types of temperature regulation devices providing a raised or a lowered local temperature environment can also be used. Thus, the temperature regulation device could also be a cooling device. The term "incubator" is used herein for convenience in describing one particular example of the system 150. However, the term is also intended to apply to other types of temperature regulation devices unless it is specifically noted otherwise or apparent from the context that the disclosure is specific to an incubator. Preferably, the system 150 includes a communication connection 154 between the incubator 152 and the humidifier 20, which can be any suitable connection using any suitable communication protocol to permit electronic communication between the incubator 152 and the humidifier 20. The connection 154 can be wired or wireless.

In the illustrated arrangement, the humidifier 20 is external of the incubator 152 and the patient interface 12 is within the incubator 152. The supply tube 24 extends from the humidifier 20, external of the incubator 152, to the patient interface 12, within the incubator 152. The supply tube 24 can be a single tube or can have a tube portion external of the incubator 152 and a tube portion within the incubator 152. The illustrated supply tube 24 includes at least one sensor (generally, 156) that is connected to the humidifier 20 by a suitable connection 160. The sensor 156 detects one or more parameters of the humidified breathing gas within the supply tube 24 (e.g., temperature and/or flow rate) and communicates that information to the humidifier 20. The humidifier 20 utilizes the information from the sensor 156 to control the temperature or humidity of the breathing gas. The sensor 156 can be located outside of the incubator 152 (sensor 156a) or inside of the incubator (sensor 156b). In some arrangements, both sensors 156a, 156b can be provided.

The illustrated arrangement also includes a heating element 162 that is capable of transferring heat energy to the flow of breathing gas within the supply tube 24. The heating element 162 is shown in schematic form in FIG. 8 as surrounding the supply tube 24, but can be contained within the wall of the supply tube 24 or otherwise integrated with the supply tube 24. The heating element 162 is powered by the humidifier 20, which can operate the heating element 162 to control the temperature of the flow of breathing gas within the supply tube 24 to compensate for heat losses, for example.

Advantageously, the illustrated system 150 permits the incubator 152 to communicate information relating to the operating conditions of the incubator 152 to the humidifier 20, which can utilize the incubator information to better control the parameters of the breathing gases delivered to the patient interface 12. For example, the humidifier 20 often has incomplete information regarding the ambient conditions along the entire supply tube 24 because the information provided by the sensor 156 is dependent upon the sensor location. In a system that includes an incubator, the location of the sensor, whether inside or outside of the incubator environment, provides an incomplete picture of the environment along the entire supply tube between the humidifier and the patient interface. Multiple sensors can be employed, such as one external of the incubator and one within the incubator, but this solution undesirably increases the cost and complexity of the system. If the sensor is located outside of the incubator, the temperature control is based on the ambient conditions outside of the incubator, which can result in overheating of the flow of breathing gas and a lowering of the humidity from a desired or target level or condensation, depending on if the temperature within the incubator is above or below the target temperature of the flow of breathing gas. If the sensor is located inside the incubator, the temperature control is based on the ambient conditions inside of the incubator, which are typically warmer than the conditions outside of the incubator. As a result, the humidifier may not provide enough heat to the breathing gas, which can result in condensation.

With the illustrated arrangement, the sensor 156 can be positioned outside of the incubator 152 and the incubator 152 can provide incubator data to the humidifier 20 to provide a more complete picture of the conditions along the relevant portions of the supply tube 24 (e.g., outside of the incubator 152 and inside of the incubator 152). Incubator data can include any relevant information that assists the humidifier 20 in providing precise control of the delivery of humidified breathing gas, such as current temperature and temperature set-point. In one arrangement, the sensor 156a is provided outside of the incubator 152, such as at the end of the portion of the supply tube 24 just before the incubator 152. Using the current temperature and/or temperature set-point, the humidifier 20 can control the temperature and humidity of the delivered breathing gas taking into consideration the conditions outside the incubator 152 (via the sensor 156a) and the conditions inside the incubator 152 (via the incubator data) to compensate for the changing conditions experienced by the flow of breathing gas from outside to inside the incubator 152. Thus, the end of breathing tube 24 temperature set-point (at the sensor 156a or end of tube portion just prior to the incubator 152) can be dynamically adjusted to compensate for the temperature drop in the portion of the supply tube 24 within the incubator 152 (i.e., the incubator extension tube), assuming that the incubator extension tube is unheated and that the incubator temperature is lower than the temperature of the breathing gas. The end of breathing tube 24 set-point can depend on incubator temperature and the gas flow rate, possibly among other factors.

In one arrangement, a second heating element 164 can be provided to apply heat energy to the flow of breathing gas within the portion of the supply tube 24 within the incubator 152 or the incubator extension tube. Preferably, the second heating element 164 is controllable by the humidifier 20 separately from the first heating element 162. Thus, the humidifier 20 can heat the gas within the incubator extension tube a different amount (different applied heat energy) relative to the gas within the portion of the supply tube 24 outside of the incubator 152. Advantageously, such an arrangement can utilize data from the sensor 156a to provide feedback control of the heating element 162 and feed forward control of the heating element 164. The feed forward control of the heating element 164 can be based on the incubator 152 current temperature or temperature set-point. Accordingly, the extra sensor 156b is not necessary, but can be provided if desired. For example, the sensor 156b may be desirable to serve as a safety back-up to the sensor 156a, or to verify temperature information from the incubator 152 or serve as a safety back-up to the sensors of the incubator 152. Such an arrangement permits precise control of the temperature and/or humidity of the flow of breathing gas within both the portion of the supply tube 24 outside of the incubator 152 and the extension tube portion of the supply tube 24 within the incubator in a cost-effective manner. The humidifier 20 could also be used to operate the incubator 152, either automatically or manually. For example, a user interface of the humidifier 20 could be utilized to allow a user of the system 150 to operate the incubator 152 over the communication connection 154. In other arrangements, the humidifier 20 could automatically send control signals to operate the incubator 152 (e.g., set an operating parameter or operating mode).

Figure 9:
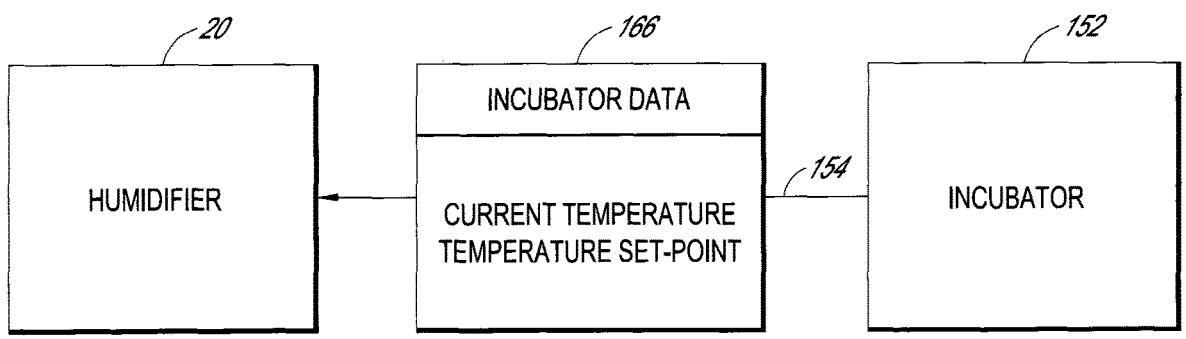
FIG. 9 illustrates a data communication connection between the flow generator and the incubator of the respiratory assistance system of FIG. 8.

FIG. 9 illustrates an example of a flow of incubator data 166 from the incubator 152 to the humidifier 20 over the communication connection 154. As illustrated at block 166, the incubator data can include any relevant information relating to an operating parameter or operating condition of the incubator 152 that can assist the humidifier 20 in precisely controlling the temperature and humidity of the flow breathing gas, including the incubator current temperature and the incubator temperature set-point. The incubator data 166 also can be transmitted to the ventilator 14 and a central monitoring system (not shown) or other remote or external memory or monitoring device, such as the central monitoring system 102 of FIG. 6.

Figure 10:
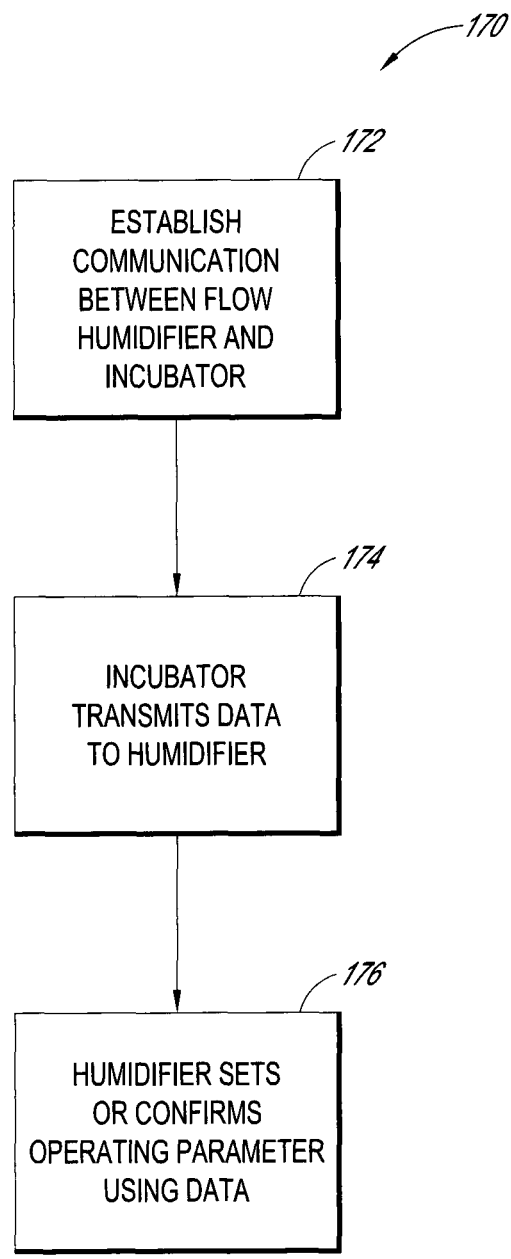
FIG. 10 illustrates a control routine for setting or confirming an operating parameter of the humidifier based on data relating to the incubator.

FIG. 10 illustrates an example of a process flow or control routine 170 for operating the humidifier 20 based on incubator data 166 transmitted from the incubator 152 to the humidifier 20. At block 172, communication is established between the humidifier 20 and the incubator 152 through any suitable method or protocol, including those described above in connection with other communication connections disclosed. At block 174, the incubator transmits incubator data 166 to the humidifier 20. At block 176, the humidifier 20 sets or confirms an operating parameter or operating mode using the data 166. The humidifier 20 can use the humidifier data along with other information (e.g., gas flow rate) to set the operating parameters (e.g., temperature within the humidifier 20 and power level of the heating elements 162 or 164). The activities of blocks 174 and 176 can be repeated as often as desired to establish a control loop.

Figure 11:
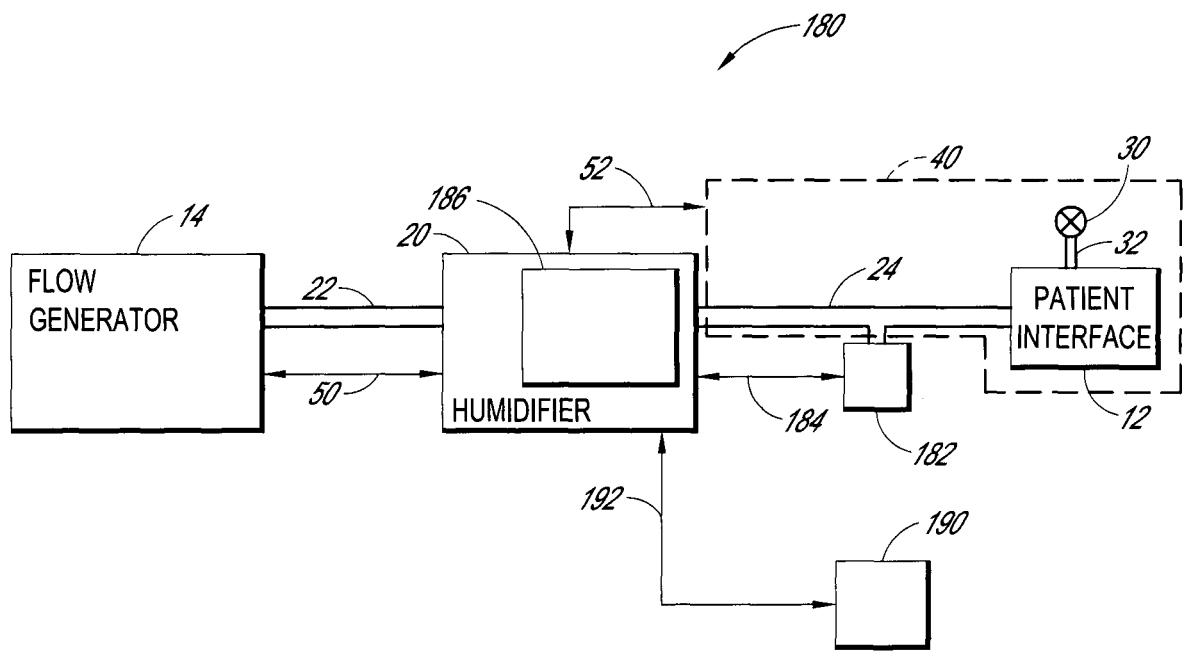
FIG. 11 illustrates a respiratory humidification system, such as a system similar to the system of FIG. 1, which incorporates peripheral devices, such as a nebulizer and/or pulse oximeter.

FIG. 11 illustrates another system 180, which preferably is similar to the systems 10, 100 and 150 described above. Accordingly, the same reference numbers are used to refer to the same or similar components. The system 180 includes a flow generator, such as a ventilator 14, which has a user interface 16. The ventilator 14 supplies a flow of breathing gas to a humidifier 20 through a supply tube 22. Although not shown, a source of breathing gas can supply breathing gas to the ventilator 14. The humidifier 20 supplies a flow of humidified breathing gas to a patient interface 12 through a supply tube 24. Although not shown, the humidifier 20 can be connected to a source of water or other fluid for refill purposes. The patient interface 12 delivers expiration gases to an expiratory tube 32. An optional expiratory pressure device 30 can be connected to the patient interface 12 by the expiratory tube 32. As described above, if provided, the expiratory pressure device 30 can be located remotely from the ventilator 14 or can be located at or can be integral with the ventilator 14, in which case the expiratory tube 32 can extend to the ventilator 14 (not shown in FIG. 11). The breathing circuit 40 can include the supply tubes 22 and 24 along with the expiratory tube 32. Preferably, the ventilator 14 and humidifier 20 are electronically connected for communication with one another by a communication connection 50. Similarly, the humidifier 20 and breathing circuit 40 preferably are electronically connected for communication with one another by a communication connection 52.

The system 180 also includes one or more additional system components that are configured for electronic communication with the humidifier 20, which can be referred to as a peripheral component or device. In the illustrated system 180, a drug delivery device, such as a nebulizer 182, is incorporated into the system 180 to deliver a substance to the breathing circuit 40 in the form of a vaporized mist. The nebulizer 182 may directly communicate with the supply tube 24 of the breathing circuit 40. The nebulizer 182 communicates with the humidifier 20 through a suitable communication connection 184, which can be wired or wireless, using any suitable communication protocol. The illustrated humidifier 20 includes a user interface 186, which preferably includes a display. The system 180 is configured such that the nebulizer 182 can transmit information relating to the operation of the nebulizer ("nebulizer data") to the humidifier 20. The humidifier 20 can receive the nebulizer data and display the data on the user interface 186. Such an arrangement can allow the nebulizer 182 to omit a user display, which can reduce the cost of the nebulizer 182 and avoid a duplication of features within the system 180. In some arrangements, the system 180 is configured to allow the humidifier 20 to send information, such as control signals, to the nebulizer 182. Accordingly, the nebulizer 182 can also omit a user interface, which can further reduce the cost of the nebulizer 182. The user interface functions can be accomplished with the user interface 186 of the humidifier 20. Similar to the operation of the prior systems 10, 100, 150, the humidifier 20 of the system 180 can utilize the nebulizer data to improve the operation of the humidifier 20 and the overall system 180. For example, the nebulizer data can include alarm conditions, such as an overheating of the nebulizer, and the humidifier 20 (or other systems components) can utilize the information, if alarm conditions or alarm functionality is provided by the particular nebulizer. In response to such information, the humidifier 20 can quickly react to shut down all heating elements to assist in reducing the heat of the nebulizer 182.

The system 180 can also include another peripheral device or component 190, which can be a measurement device, such as a pulse oximeter, for example. The pulse oximeter 190 can communicate with the humidifier 20 through a suitable communication connection 192, which can be wired or wireless, using any suitable communication protocol. Similar to the nebulizer 182, the pulse oximeter 190 can utilize the user interface 186 of the humidifier 20, which can permit display of pulse oximeter 190 information or data and, if desired, permit setting of parameters of the pulse oximeter 190 without requiring the pulse oximeter 190 to have its own user interface. The pulse oximeter 190 data can include oxygen saturation (SpO2), among other relevant data. Such an arrangement can reduce the cost of the pulse oximeter 190 while maintaining or improving functionality. The humidifier 20 can also transmit data regarding any peripheral device, such as the nebulizer 182 and pulse oximeter 190, to the ventilator 14, which can utilize the data to control operating parameters of the ventilator 14 or to publish the data to another component or system, such as a central monitoring system or patient records system, for example. In an alternative arrangement, the peripheral devices 182, 190 (or any other peripheral device) could be configured for communication with the ventilator 14 or other system component that includes a user interface in the place of, or in addition to, the humidifier 20.

Figure 12:
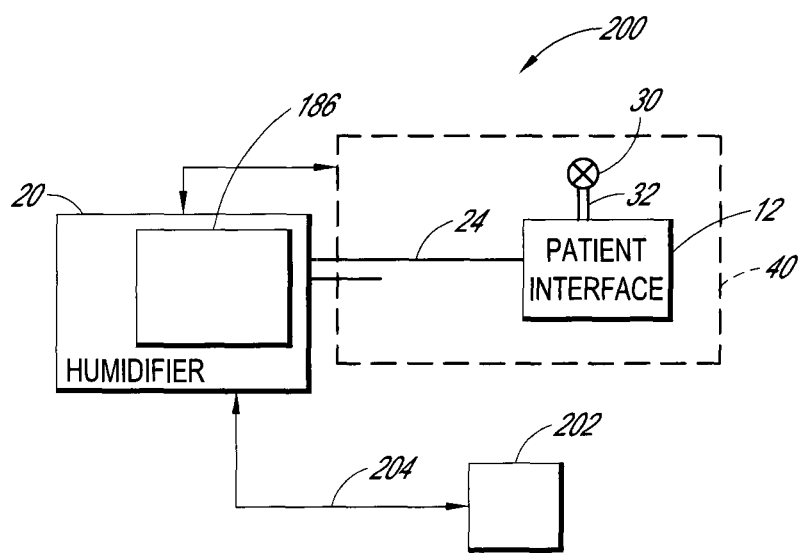
FIG. 12 illustrates a respiratory humidification system including a humidifier, a breathing circuit and a peripheral device.

FIG. 12 illustrates another system 200, which is similar to the system 180, but omits the ventilator 14. In the system 200, the humidifier 20 can simply provide humidified ambient or room air to the patient interface 12. The humidifier 20 could have an internal flow source to generate a flow of air or other gas. Alternatively, a flow of breathing gas can be provided by a non-electronic source of breathing gas, such as a mechanical flow regulator or gas blender, gas bottle, or a gas wall source, for example. In other respects, the system 200 preferably is similar to the system 180 and permits communication of a peripheral device 202 with the humidifier 20 through a suitable communication connection 204 using any suitable communication protocol.

Figure 13:
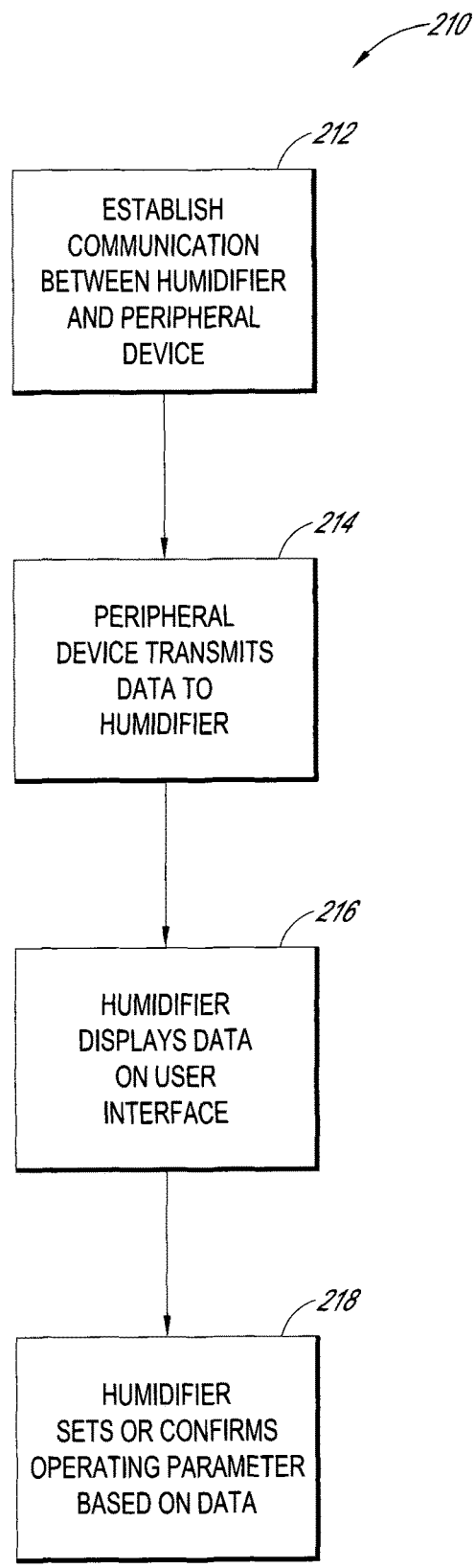
FIG. 13 illustrates a control routine for displaying data relating to the peripheral device on an interface of the humidifier and/or setting or confirming an operating parameter of the peripheral device using the interface of the humidifier in the system of FIG. 12.

FIG. 13 illustrates an example of a process flow or control routine 210 for displaying data or allowing control of the peripheral device 182, 190, 202 or allowing the humidifier 20 to operate on the basis of the data in the system 180 of FIG. 11 or system 200 of FIG. 12. At block 212, communication is established between the humidifier 20 and the peripheral device 182, 190, 202 using any suitable method or protocol, such as those described above. At block 214, the peripheral device 182, 190, 202 transmits data to the humidifier 20, which can include any relevant information relating to the operation of the peripheral device 182, 190, 202. At block 216, if appropriate, the humidifier 20 displays some or all of the peripheral device data on the user interface 186 of the humidifier 20. At block 218, if appropriate, the humidifier 20 can set or confirm an operating parameter or operating mode based on the peripheral device data. For example, if the peripheral device is a nebulizer 182, the nebulizer data can include alarm conditions (e.g., overheating of the nebulizer) and in response, the humidifier 20 can take appropriate action (e.g., shut down heating elements). In addition, the user interface 186 of the humidifier 20 can be utilized to set a parameter of the peripheral device 182, 190, 202.

In some of the systems disclosed herein, the flow generator is described as a ventilator for the sake of example. However, the systems can include any type of ventilator or any other type of flow generator that is capable of delivering a flow of breathing gas. For example, the flow generator can be a continuous positive airway pressure (CPAP) machine, variable or bi-level positive airway pressure (VPAP or BPAP) machine, an infant respirator, or a machine that is capable of operating in one or more of such modes. The flow generator could also be an electronic gas blender, bottled gas or gas from wall source, for example. Thus, the use of the term ventilator herein is by way of example and not limitation.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present systems have been described in the context of particularly preferred embodiments, the skilled artisan will appreciate, in view of the present disclosure, that certain advantages, features and aspects of the systems may be realized in a variety of other applications, many of which have been noted above. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

Through the description and the claims, the terms "comprises", "comprising" and the like are to be construed in an inclusive sense, that is, in the sense of "including but not limited to", unless the context clearly requires otherwise.

Although the invention has been described by way of example and with reference to possible embodiments thereof, it is to be understood that modifications or improvements may be made thereto without departing from the spirit and scope of the invention and without diminishing its attendant advantages. Furthermore, where reference has been made to specific components or integers of the invention having known equivalents, such equivalents are herein incorporated as if individually set forth.

Any discussion of the prior art throughout the specification should in no way be considered as an admission that such prior art is widely known or forms part of the common general knowledge in the field anywhere in the world.

What is claimed is:

1. A respiratory humidification system, comprising:
    a humidifier comprising a humidifier unit and a humidity chamber that outputs a humidified flow of breathing gas;
    a breathing circuit that receives the flow of humidified breathing gas from the humidifier;
    a patient interface that receives the flow of humidified breathing gas from the breathing circuit and delivers the flow of humidified breathing gas to a patient;
    a peripheral device selected from the group consisting of a nebulizer, a pulse oximeter, and an incubator; and
    a communication connection configured to permit electronic communication between the peripheral device and the humidifier.

2. The respiratory humidification system of claim 1, wherein the humidifier sets an operating parameter or mode of the humidifier based on data from the peripheral device.

3. The respiratory humidification system of claim 1, wherein the peripheral device is the nebulizer and the humidifier is configured to send a control signal to the nebulizer to control operation of the nebulizer.

4. The respiratory humidification system of claim 1, wherein the peripheral device is the nebulizer and humidifier operating parameters are configured to be set based on a type of the nebulizer.

5. The respiratory humidification system of claim 1, wherein the humidifier comprises a user interface and the humidifier displays data from the peripheral device on the user interface.

6. The respiratory humidification system of claim 5, wherein the humidifier is configured to permit a user to set an operating parameter or mode of the peripheral device using the user interface.

7. The respiratory humidification system of claim 1 further comprising a sensor, wherein data from the sensor comprises one or more of: a flow rate and a temperature of the flow of humidified breathing gas.

8. The respiratory humidification system of claim 7, wherein the peripheral device is the incubator and the data from the incubator comprises one or more of: a current temperature and a set-point temperature of the incubator.

9. The respiratory humidification system of claim 7, wherein the peripheral device is the incubator, the breathing circuit comprises a first portion located outside of the incubator and a second portion located within the incubator, a first heating element is configured to apply heat energy to the first portion, a second heating element is configured to apply heat energy to the second portion, and a second sensor is configured to detect a parameter of the flow of humidified breathing gas, the second sensor located within the first portion.

10. The respiratory humidification system of claim 1, wherein the peripheral device is the incubator and the humidifier is located outside of the incubator.

11. The respiratory humidification system of claim 10, wherein the patient interface is located within the incubator.

12. The respiratory humidification system of claim 11, wherein the breathing circuit extends between the humidifier and the patient interface.

13. The respiratory humidification system of claim 1, wherein the peripheral device is the incubator, the breathing circuit comprises a first portion located outside of the incubator and a second portion located within the incubator, a first heating element is configured to apply heat energy to the first portion, a second heating element is configured to apply heat energy to the second portion, and a sensor is configured to detect a parameter of the flow of humidified breathing gas, the sensor located within the first portion.

14. The respiratory humidification system of claim 13, wherein the humidifier controls the first heating element and the second heating element utilizing data from the sensor and data from the incubator.

15. The respiratory humidification system of claim 1, wherein the peripheral device is the nebulizer and data from the nebulizer is transmitted from the nebulizer to the humidifier.

16. The respiratory humidification system of claim 15, wherein the data from the nebulizer comprises alarm conditions.

* * * * *